US00PP35333P2

(12) United States Plant Patent
Hansen

(10) Patent No.: US PP35,333 P2
(45) Date of Patent: Aug. 22, 2023

(54) ***ALLIUM* PLANT NAMED 'BUBBLE BATH'**

(50) Latin Name: *Allium hybrid (Linnaeus)*
Varietal Denomination: Bubble Bath

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,930

(22) Filed: Jan. 26, 2023

(51) Int. Cl.
*A01H 5/02* (2018.01)
*A01H 6/04* (2018.01)

(52) U.S. Cl.
USPC ..... Plt./263.1
CPC ..... *A01H 6/045* (2018.05)

(58) Field of Classification Search
USPC ..... Plt./263.1
CPC ..... A01H 6/045; A01H 5/02
See application file for complete search history.

*Primary Examiner* — Keith O. Robinson

(57) ABSTRACT

A new and distinct cultivar of *Allium* ornamental onion plant named 'Bubble Bath' is a large upright habit, with glaucous, stiff, broad, strap-like, upright, flattened, gray-green foliage with slight longitudinal twisting, and numerous, tightly-clustered, light lavender flowers forming a large, globose, upright umbels. The new plant is useful for containers, landscaping and cut flowers.

2 Drawing Sheets

Botanical classification: *Allium* hybrid (Linnaeus).
Variety denomination: 'Bubble Bath'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2022. No plants of *Allium* 'Bubble Bath' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to the new and distinct ornamental onion, *Allium* 'Bubble Bath' was developed by the inventor at a wholesale perennial nursery in Zeeland, Mich., USA as the result a greenhouse cross of proprietary unreleased selection known as 14-SP-ALL-311 (not patented) and 'Nor'easter' (not patented) on Jun. 23, 2014. Seeds from this pollination were collected in fall of 2014 and were sown later that same year. The plant was originally selected in the summer of 2016 and given the breeder code 14-1-1.

*Allium* 'Bubble Bath' has been successfully asexually propagated by division method since 2016 at a wholesale perennial nursery in Zeeland, Mich., and was found to be stable and produce identical plants that maintain the unique characteristics of the original plant through multiple generations.

SUMMARY OF THE PLANT

*Allium* 'Bubble Bath' differs from its parents as well as all other ornamental onion known to the applicant. The most similar known *Allium* cultivars are: 'Serendipity' U.S. Plant Pat. No. 32,023, 'Millenium' (not patented), and 'Blue Eddy' (not patented).

'Blue Eddy' has a much shorter habit, smaller and more curved leaves, smaller flower globes, and light lilac-pink-colored flowers, flowering much later in the season. 'Millenium' has a smaller habit, darker rosy-purple flowers beginning about the same time as the new plant, and less-glaucous green leaves. 'Serendipity' has a smaller habit, darker rosy-purple flowers and begins flowering about two weeks later than the new plant.

The female parent has narrower, glossy, green leaves with smaller inflorescences of darker purple flowers. The male parent has wider foliage and white flowers on larger inflorescences.

*Allium* 'Bubble Bath' differs from these above cultivars and all unregistered cultivars known to the inventor in the following combined traits:

1. Glaucous, upright, stiff, broad, strap-like, flattened, gray-green foliage with slight longitudinal twisting;
2. Moderately compact habit, drought tolerant, rabbit and deer resistant, medium-sized clumps;
3. Numerous, tightly-clustered, light-lavender flowers forming a large, dense, globose umbel;
4. Strong stems hold flower head globes upright through flowering and seed production.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
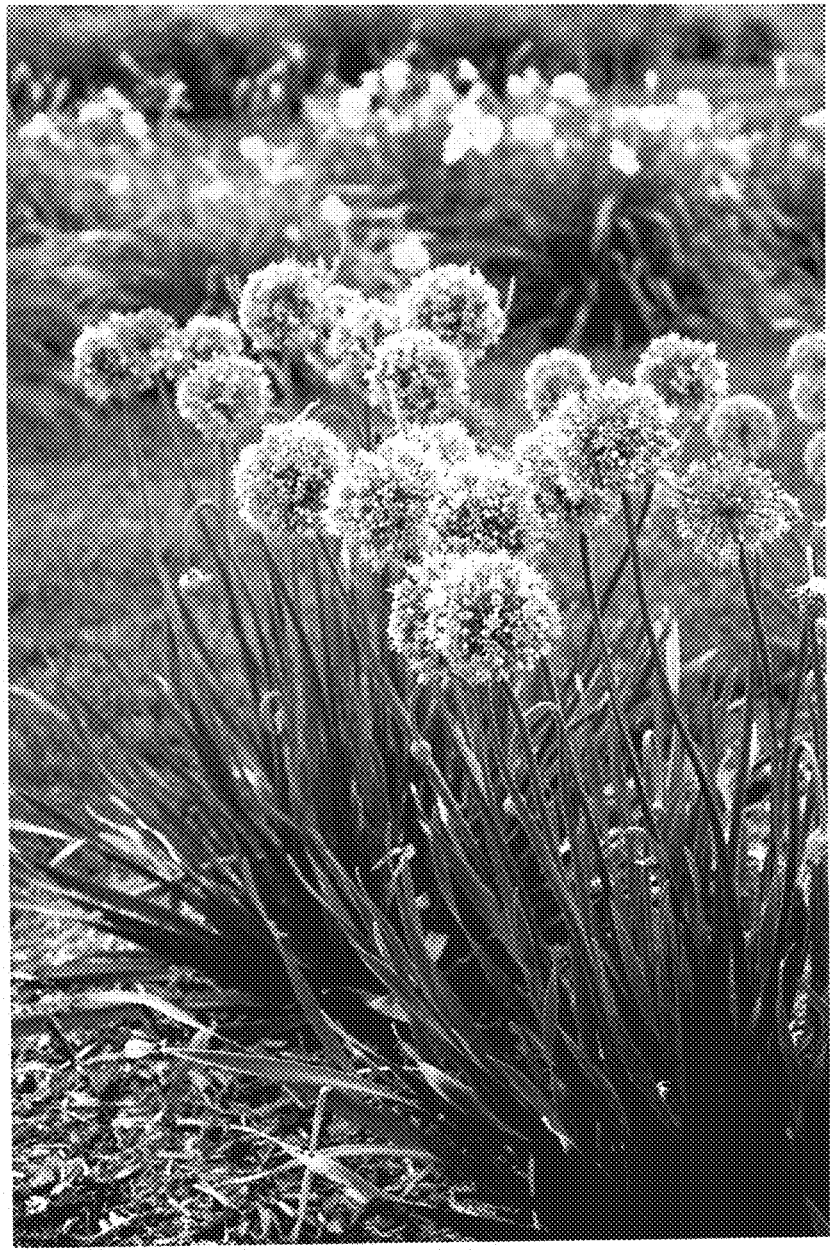
FIG. 1 shows the side-view habit of a three-year-old plant in early flowering.
Figure 2:
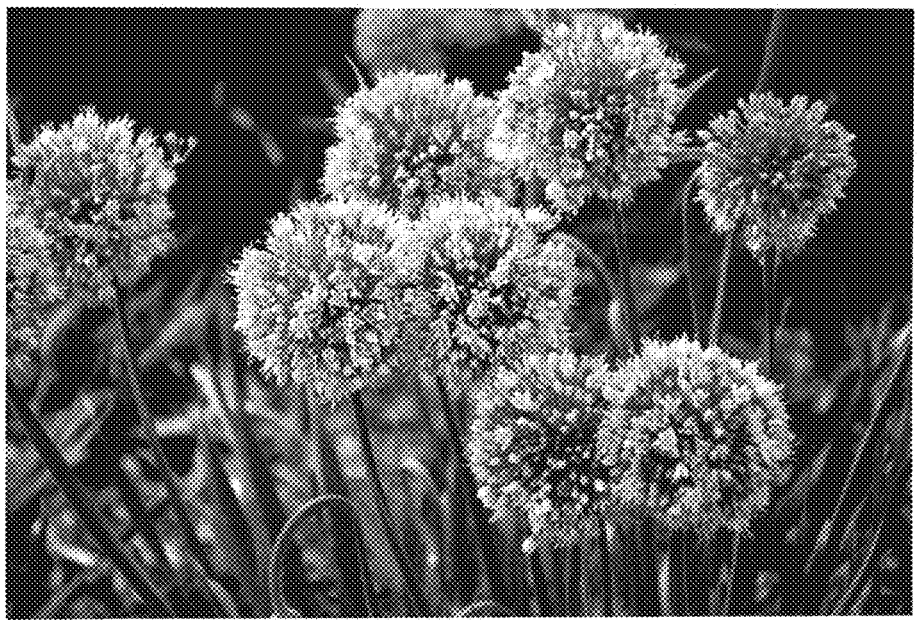
FIG. 2 shows a close-up of the umbel with flowers and buds.

The following descriptions and color references are based on the 2015 edition of The Royal Horticultural Society Colour Chart except where common dictionary terms are used. The new plant, *Allium* 'Bubble Bath', has not been observed under all possible environments. The phenotype may vary slightly with different environmental conditions, such as temperature, light, fertility, moisture, and maturity levels, but without any change in the genotype. The following observations and size descriptions are of a three-year-old plant in a display garden of a wholesale perennial nursery in Zeeland, Mich. under full sun with supplemental water and fertilizer as needed.

Botanical classification: *Allium* hybrid;

Parentage: Female or seed parent was 14-SP-ALL-311, the male or pollen parent was 'Nor'easter';

Propagation method: By division;

Growth rate: Vigorous, flowering in 4-liter containers in about 12 weeks;

Rooting habit: Fibrous from base of bulbs, lightly branching; color nearest RHS 158C;

Plant habit description: Dense clump of bulbs with sessile rosulate foliage about 90 cm across and about 48 cm tall; flowering to about 84 cm tall and inflorescences to about 106 cm across;

Bulbs: Elongated conical shape; about 7 cm long and 1.5 cm diameter at base; average about 42 per plant; color nearest RHS 155D;

Leaves: Sessile; linear; glaucous, glabrous dull surfaces; semi-succulent; simple; margin entire; sharply acute apex, truncate base; slightly twisted longitudinally nearly 360°; mostly flat; about 47 cm long, about 14 mm across near middle and to about 3 mm thick near middle; arranged in two-ranked tuffs from bulb; about 12 leaves per bulb; fragrance onion-scented;

Leaf color: Expanding adaxial and abaxial nearest RHS 138B; mature adaxial and abaxial between RHS N138B and RHS 137A distally with basal one-eighth transitioning to nearest RHS 145D;

Leaf venation: Parallel; color same as leaf abaxial and adaxial;

Inflorescence: In dense terminal umbel; about 350 to 450 flowers per inflorescence; to about 63 and an average of about 42 inflorescences per plant; globose, about 9 cm across and about 9 cm tall, rarely with satellite projections of four to six flowers on a single pedicel base extending an additional 2 cm; lasting about five weeks; onion-like fragrance; beginning in mid-July to mid-August in Michigan and continuing for three weeks;

Blooming habit: One terminal umbel inflorescence per stem; with upright globe in bud, remaining upright as initial flowers open;

Flowers: Campanulate; incomplete; perfect; with two sets of three tepals, outer set smaller than inner; inferior ovary; actinomorphic; upward, outwardly, and drooping attitude depending on position in umbel; individually effective about four to six days; from base to exerted stamens to about 12 mm long and corolla to about 12 mm across;

Tepals (outer set): ovate to deltoid; convex; glabrous; lustrous; acute apex, fused truncate base; about 6.5 mm long and about 3.5 m across;

Tepal (inner set): Ovate to deltoid; flat; glabrous; lustrous; acute apex, broadly acute base; about 8 mm long and to about 4 mm across;

Tepal color (inner and outer sets identical): Adaxial nearest RHS 84D, abaxial nearest RHS 84D;

Buds one day prior to opening: Globose slightly flattened on three sides; rounded base, rounded apex; about 8 mm long and about 5.5 mm diameter at widest point near middle;

Bud color: Variable; with some tepal midribs nearest RHS N75A and other midribs nearest RHS N75C and tepal margins between RHS 84D and RHS NN155D;

Pedicel: Cylindrical; stiff; upward, outwardly, and drooping depending on orientation in umbel; glabrous; glaucous; about 25 mm long and about 0.5 mm diameter;

Pedicel color: Nearest RHS 138A;

Peduncle: Glabrous, glaucous; flattened trapezoid to nearly ovoidal with two wings in cross-section; to about 62.5 cm long, base about 11 mm wide and about 7 mm thick;

Peduncle color: Basal 5 to 10 cm nearest RHS 138A, distally nearest RHS N138A;

Gynoecium: Pistil single; to about 12.5 mm long;

*Style*.—Single; cylindrical; glabrous; elongating after flower opening to about 7 mm long, about 0.5 mm across when mature; color between RHS 84D and RHS NN155D.

*Stigma*.—Globose; about 0.2 mm across; color nearest RHS NN155C.

*Ovary*.—Distinctly tri-loculed; obcordate, wider at apex and slightly narrower at base; about 3 mm long and 3.5 mm across at acute apex and 3 mm across at truncate base; color between RHS 84D and RHS NN155D at apex and nearest RHS NN155D at base.

Androecium: Typically, six, rarely seven; exserted to about 11 mm long;

*Anther*.—Oblong; about 2 mm long and about 1 mm wide; basifixed; longitudinal; color between RHS 197C and RHS N187C.

*Filament*.—Exserted; glabrous; cylindrical distally, flattened in proximal 3 mm; to about 10 mm long and 3 mm across at base and about 0.5 mm diameter below anther; color nearest RHS 84D distally and lightening to nearest RHS NN155D at base.

*Pollen*.—Abundant; color nearest RHS 11C.

Fruit: Tri-valved loculicidal capsule; about 6.0 mm long and 4.5 mm across; typically dehiscing to within about 1.0 mm of base; one to three seeded; color upon maturity nearest RHS 199D;

Seed: Prolific; elliptic, flattened along one long side; about 2.5 mm long and about 1.5 mm across; color nearest RHS 202A;

Disease and pest resistance: Ornamental onions typically resist deer and rabbit feeding. Resistance beyond that of other ornamental onions has not been observed. *Allium* 'Bubble Bath' plant grows best with good drainage and is able to tolerate some drought when established. Winter hardiness at least from USDA zone 4 through 8.

I claim:

1. A new and distinct cultivar of *Allium* plant named 'Bubble Bath' as herein described and illustrated.

* * * * *